(12) United States Patent
Garcia

(10) Patent No.: US 10,675,185 B2
(45) Date of Patent: Jun. 9, 2020

(54) GOGGLE LENS SYSTEMS

(71) Applicant: Daniel Carl Garcia, Parker, CO (US)

(72) Inventor: Daniel Carl Garcia, Parker, CO (US)

(*) Notice: Subject to any disclaimer, the term of this patent is extended or adjusted under 35 U.S.C. 154(b) by 14 days.

(21) Appl. No.: 15/490,365

(22) Filed: Apr. 18, 2017

(65) Prior Publication Data

US 2018/0296393 A1 Oct. 18, 2018

(51) Int. Cl.
*A61F 9/02* (2006.01)

(52) U.S. Cl.
CPC .............. *A61F 9/025* (2013.01); *A61F 9/027* (2013.01); *A61F 9/029* (2013.01)

(58) Field of Classification Search
CPC .......... A61F 9/025; A61F 9/027; A61F 9/028; A61F 9/026; A61F 9/029
See application file for complete search history.

(56) References Cited

U.S. PATENT DOCUMENTS

| | | | |
|---|---|---|---|
| 4,138,746 A * | 2/1979 | Bergmann | A42B 3/26 2/10 |
| 4,455,689 A | 6/1984 | Boyer | |
| 4,563,065 A * | 1/1986 | Kreissl | A61F 9/025 351/47 |
| 4,716,601 A * | 1/1988 | McNeal | A61F 9/025 2/434 |
| 5,592,698 A * | 1/1997 | Woods | A42B 3/26 2/424 |
| 6,085,358 A * | 7/2000 | Cogan | A42B 3/26 2/424 |
| 6,388,813 B1 * | 5/2002 | Wilson | A42B 3/26 359/630 |
| 9,161,858 B2 * | 10/2015 | Capers | A42B 3/26 |
| 2003/0110552 A1 * | 6/2003 | Youmans | A61F 9/028 2/426 |
| 2009/0229044 A1 * | 9/2009 | Gill | A42B 3/26 2/434 |
| 2014/0057074 A1 * | 2/2014 | McInturff | A61F 9/025 |
| 2015/0328050 A1 * | 11/2015 | Sigismondo | A61F 9/025 2/434 |
| 2017/0071792 A1 * | 3/2017 | Wilson | A61F 9/029 |

* cited by examiner

*Primary Examiner* — Khaled Annis
(74) *Attorney, Agent, or Firm* — Mohr Intellectual Property Law Solutions, PC

(57) ABSTRACT

Removable goggle lens system including a sequentially-stacked set of lenses each of the lenses having a front-face, a back-face, a thickness, and a finger-tab. Each of the lenses are defined by the front-face, the back-face, the front-face, and the back-face separated by the thickness; and the finger-tab formed as an extension of the thickness such that a wearer-user can remove each of the lenses sequentially as desired approaching a main lens of a host goggle as sequentially removed.

20 Claims, 5 Drawing Sheets

GOGGLE LENS SYSTEMS

BACKGROUND

The present disclosure relates generally to goggle accessories. In particular, goggle lens systems are described.

Known goggle accessories are not entirely satisfactory for the range of applications in which they are employed. For example, existing goggle lens for use in motorsports are not easy to manipulate during use. In addition, conventional goggles can become dirty and scratched during rough use. Dirt and debris can accumulate between the lens and the goggle using existing systems which is undesirable since it impairs the vision of the rider. Scratches caused during use or cleaning may damage the goggle(s) for future use. Streaking left from cleaning is also undesirable. For riders using 'stacked' tear-off film versions it is not uncommon for the rider to accidently grab and remove the entire stack of removable lenses which is not desirable.

The current tear-off system available is a two-part system, part-1) the typical goggle main lens can be flat or pre-curved, part-2) the goggle tear off film is a set of flat stacked single or laminated poly film that is manually secured onto the goggle's main lens. The problem with this system is that it allows moisture, dust, sand, mud and debris to collect between the single tear-off films and (or) between the main lens and the tear-off stack. Another problem with this system is when the laminated or single stack of tear-off film(s) are secured to the goggle's main lens the clarity of lens is then distorted because the tear-off films are flat and when secured to a curved main lens the user's vision is then distorted & impaired. Yet another problem is that the individual tabs that are folded in an alternating way allows the user to remove a single layer of film from the stack during use often leads to the user accidently grabbing the entire folded stack and removing the entire stack when in use thus leaving the user without a tear-off system.

Thus, there exists a need for goggle lens systems that improve upon and advance the design of known goggle accessories. Examples of new and useful goggle accessories relevant to the needs existing in the field are discussed below.

Disclosure addressing one or more of the identified existing needs is provided in the detailed description below. Examples of references relevant to goggle lens accessories include U.S. Pat. No. 4,455,689. The complete disclosures of the above patents and patent applications are herein incorporated by reference for all purposes.

SUMMARY

The present disclosure is directed to a removable goggle lens system including a sequentially-stacked set of lenses each of the lenses having a front-face, a back-face, a thickness, and a finger-tab. Each of the lenses are preferably pre-curved and defined by the front-face, the back-face; the front-face and the back-face separated by the thickness, and the finger-tab formed as an extension of the thickness such that a wearer-user can remove each of the lenses sequentially as desired approaching a main lens of a host goggle as sequentially removed. In some examples, goggle lens system includes a 180 degree view goggle having a goggle-frame including; a lens track comprising rigid, yet flexible rubber, a main lens, a headstrap, and at least one removable lens. In some further examples, goggle lens system includes a 180 degree view goggle having a goggle-frame including a lens track comprising rigid, yet flexible rubber, and vent ports and vent-port covers, a main lens, a headstrap comprising an applied flexible anti-slipping means, and a plurality of sequentially stacked removable lens. The purpose of the present invention is to improve off-road goggles and laminated tear-offs and function of the goggle.

DETAILED DESCRIPTION

Figure 1:
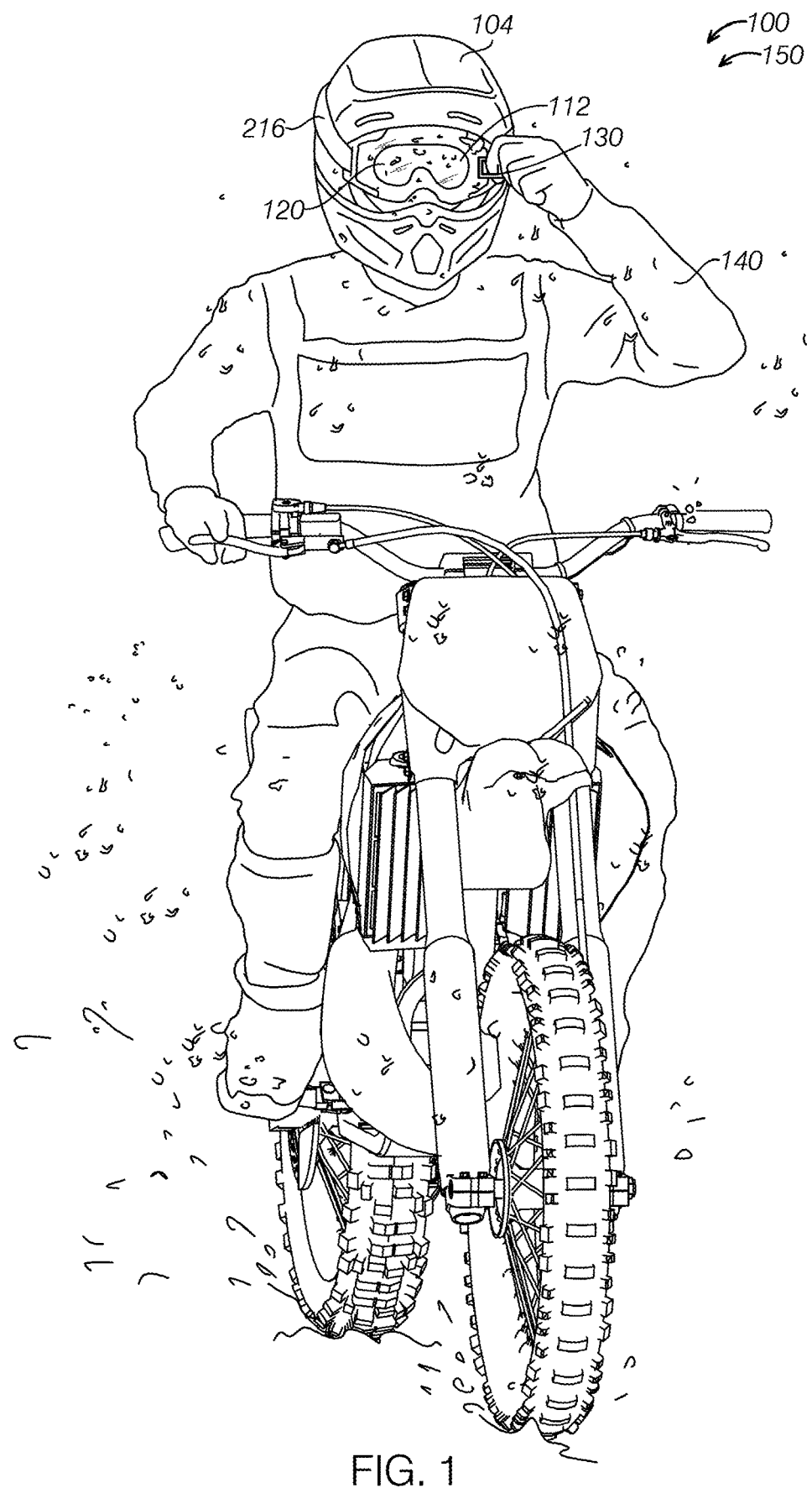
FIG. 1 is a perspective view of a first example of a goggle lens system in an in-use condition.

The disclosed goggle lens systems will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various goggle lens systems are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

This present invention will eliminate the afore mentioned problems users are known to have, the improvement will comprise of a main goggle frame hard or flexible frame, extended to a wide range view on each side to allow the rider 180 degree view with no obstruction, the rear of the goggle frame assembly comprises of layered foam and moisture whisking outer attached to the goggle frame layer to conform a comfortable fit to user. The frame is manufactured to accept the removable lens into the main frame; the frame will also comprise of a tear-off tab track delivery system manufactured directly to the goggle frame, this tear-off tab track delivery system will hold the folded tabs during operation and thus only allowing a single unfolded layer of film to be exposed and allowing the user of the goggle to only remove that exposed single layer of film from the main lens, thus eliminating the user from accidently grabbing the entire layered stack from the removable goggle lens.

The goggle will also comprise of a removable layered tear-off lens system with a variety count of layered film that is manufactured and fused directly to each other and the main lens, the main lens and layered tear-off stack of film is fused together as a single component, thus eliminating elements collecting between the main goggle lens and layers of film. The removable layered tear-off lens system is manufactured to a pre-curved form thus eliminating distorted user view through the goggle lens. The goggle frame also comprises of an attached head strap made of stretchable materials and a anti slip stripping applied to the inside of the material to eliminate the strap from slipping on the user's helmet.

With reference to FIGS. 1-9, a first example of a goggle lens systems 100, goggle lens systems 100, will now be described. Goggle lens systems 100 functions to provide a wearer-user 140 with the option to remove each of the lenses 120 sequentially as desired approaching a main lens 122 of a host goggle 112 as sequentially removed. The reader will appreciate from the figures and description below that goggle lens systems 100 addresses shortcomings of conventional goggle lens accessories. In a first embodiment, a removable goggle lens system 100 is disclosed comprising a sequentially-stacked set of lenses 120 each of the lenses 120 comprising a front-face 124, a back-face 125, a thickness, and a finger-tab. Each of the lenses are defined by the front-face 124, the back-face 125; the front-face 124, and the back-face 125 separated by the thickness 126, and the finger-tab 130 formed as an extension of the thickness 126 such that a wearer-user 140 can remove each of the lenses 120 sequentially as desired approaching a main lens 122 of a host goggle 112 as sequentially removed. Wearer-user 140 is shown in FIG. 1 wearing goggle(s) 112.

The lenses 120 are a transparent-laminate and the finger-tab 130 is folded under the back-face 125 until a top-placed (adjacent the lens 120) is removed from use whereby the finger-tab 130 then becomes accessible for pulling. A terminal lens 120 (last to be removed) is film-fused directly to the main lens 122 of a host goggle 112. The lenses 120 are a non-transparent-laminate construction. The finger-tab 130 may comprise an aperture 132. The finger-tab 130 is a pull-tab and rotates from adjacent the back-face 125 towards the front-face 124 when unfolded for a 'next-use'. An unfolding rotation ends when the finger-tab 130 has sufficiently rotated to be substantially parallel to the main lens 122. The sequentially-stacked set of lenses 120 are disposed of as removed (one by one) from the host goggle 112 via a tearing-action (pulling off from a coupled condition and thrown away).

Figure 2:
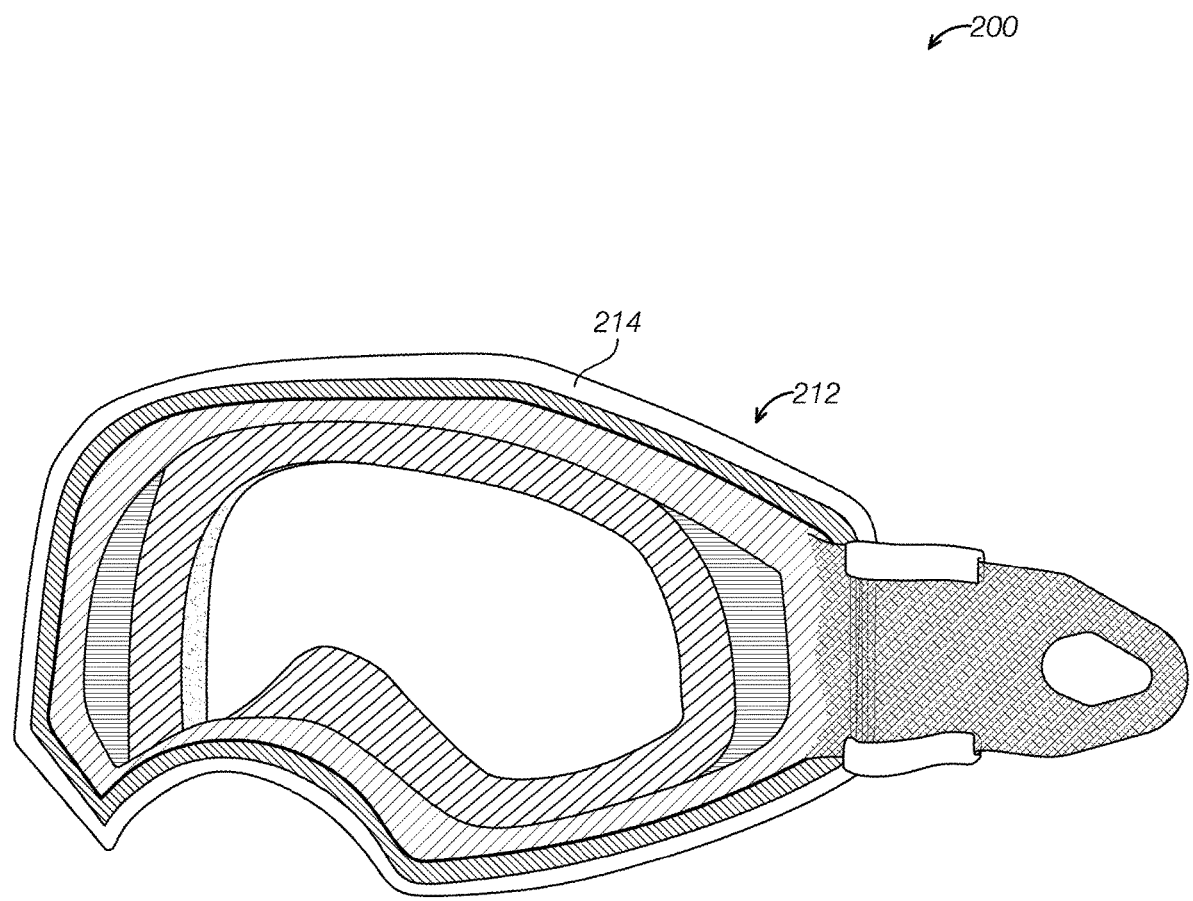
FIG. 2 is another perspective view of 180 degree view goggles of the goggle lens system.
Figure 3:
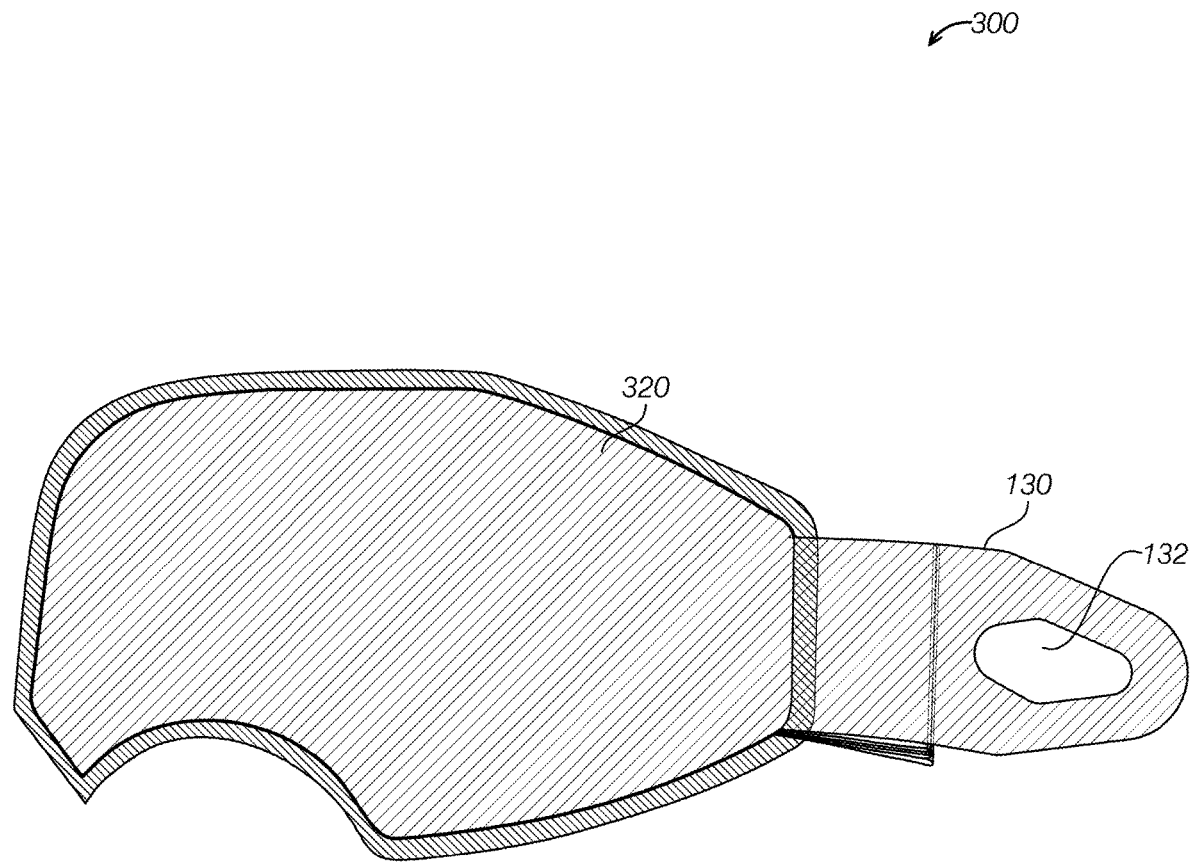
FIG. 3 is a perspective view of the 180 degree view goggles of the goggle lens system depicting a curved profile of the curved removable lens and a finger-tab.
Figure 4:
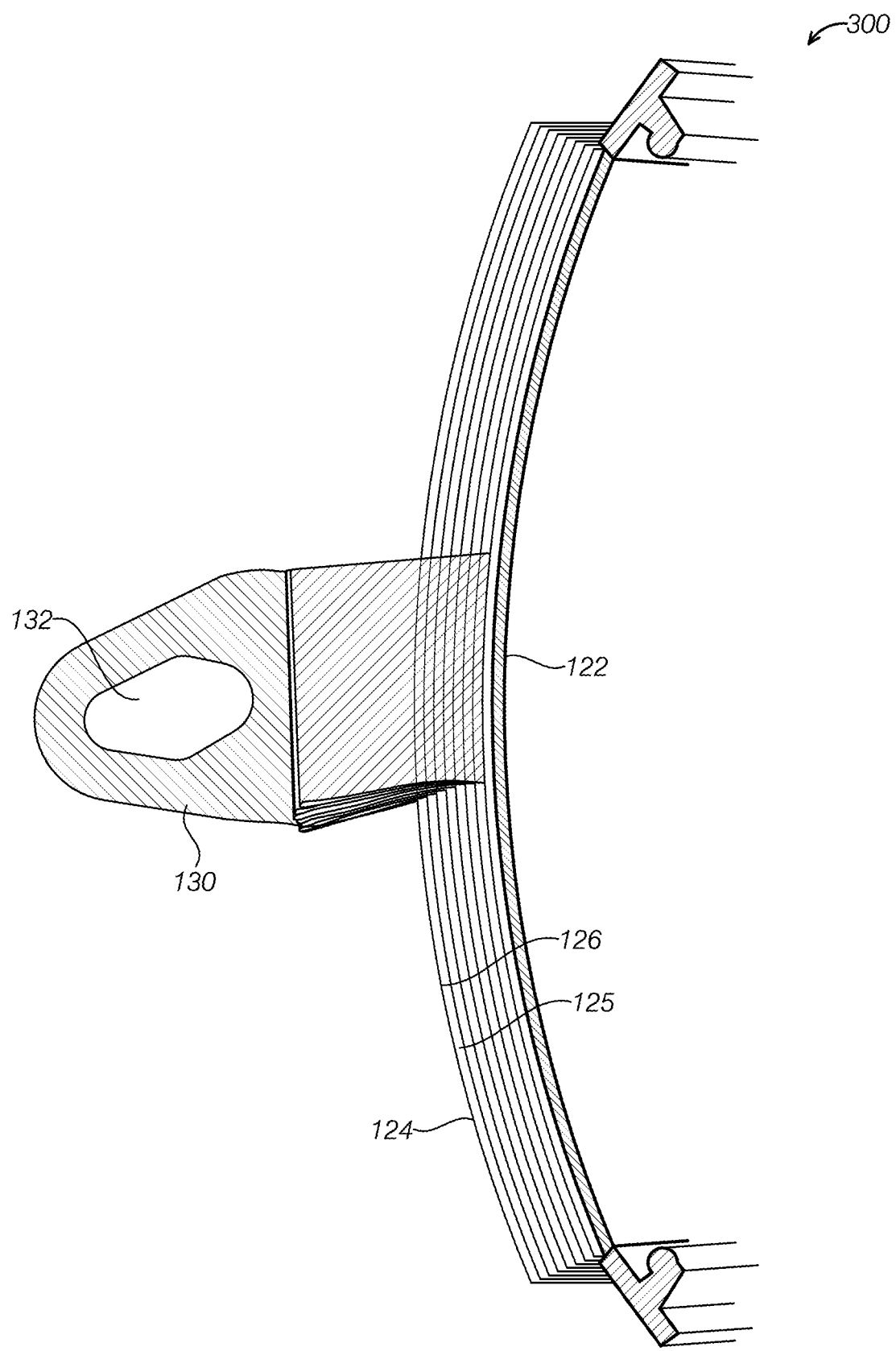
FIG. 4 is a side view of the 180 degree view goggles of the goggle lens system depicting a curved profile of the curved removable lens and a finger-tab with an aperture in a ready for use position.
Figure 5:
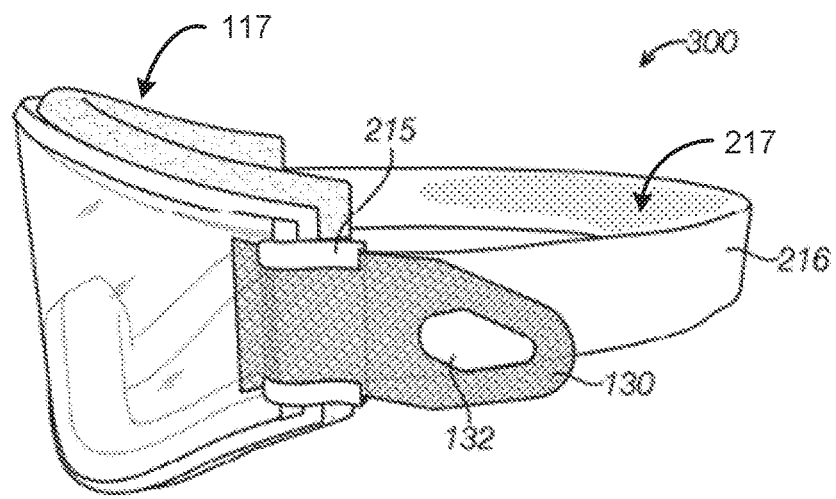
FIG. 5 is a side view of the 180 degree view goggles of the goggle lens system depicting a curved profile of the curved removable lens and a finger-tab in relation to a lens track of a track delivery system.

Turning attention to FIG. 2, a second example of a goggle lens systems 200, goggle lens systems 200, will now be described. Goggle lens systems 200 includes many similar or identical features to goggle lens systems 100. Thus, for the sake of brevity, each feature of goggle lens systems 200 will not be redundantly explained. Rather, key distinctions between goggle lens systems 200 and goggle lens systems 100 will be described in detail and the reader should reference the discussion above for features substantially similar between the two goggle lens systems (100, 200).

Figure 6:
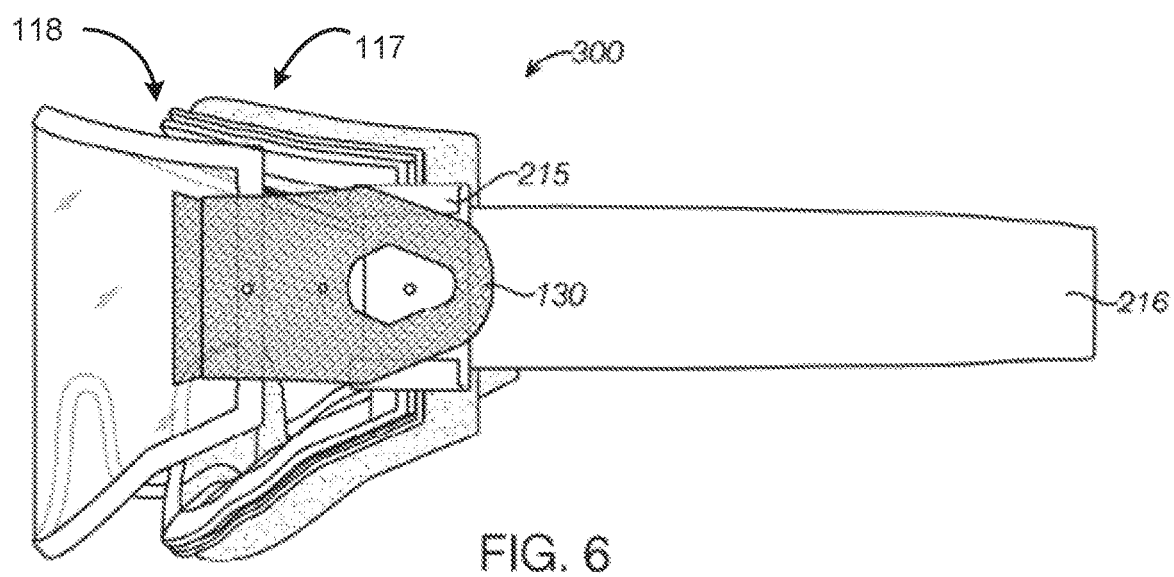
FIG. 6 is a side view of the 180 degree view goggles of the goggle lens system with the main lens set forwardly to show relative placement and a finger-tab in relation to a lens track of the track delivery system.
Figure 7:
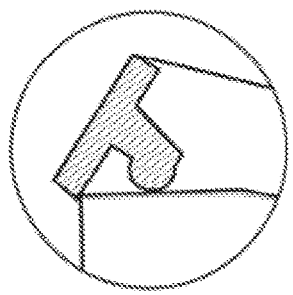
FIG. 7 is a side view of the goggle lens system.
Figure 8:
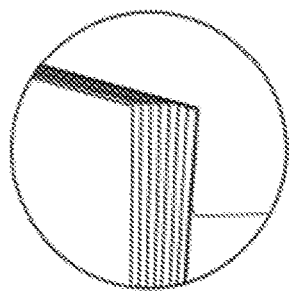
FIG. 8 is a side view of the stacked relationship of lens in the goggle lens system.
Figure 9:
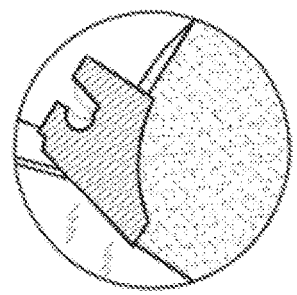
FIG. 9 is a side view of the goggle lens system.

Another embodiment is disclosed herein comprising a goggle lens system 200, comprising a 180 degree view goggle 212 having a goggle-frame 214 including a lens track 215 preferably comprising rigid, yet flexible rubber, a main lens 122, a headstrap 216, and at least one removable lens 120, as shown in FIGS. 6-7. The 180 degree view goggle 212 comprises in functional combination the goggle-frame 214, the main lens 122, the headstrap, 216 and the at least one removable lens 120.

The lens track 215 provides a mount for the main lens 122; the main lens 122 having the at least one removable lens 120 coupled thereto for removal during sport-use. The headstrap 216 couples the 180 degree view goggle 212 to a helmet 104 of a wearer-user 140 such that the wearer-user 140 can individually tear-remove each of the at least one removable lens 120 sequentially as desired approaching the main lens 122 as the at least one removable lens 120 are sequentially removed one by one.

The removable goggle lens system 200 further comprises vent ports 117. The vent ports 117 comprise breathable foam. The vent ports 117 further comprise vent-port covers 118 useful during inclement conditions to prevent water from entering from a top of the 180 degree view goggle 212. The removable goggle lens system 200 further comprise a layered foam pad attached to the goggle-frame 214 suitable for wicking moisture to promote comfort of the wearer-user 140. The headstrap 216 comprises an anti-slip strip 217 (an anti-slip stripping 217 is applied to said headstrap 216) to prevent slippage relative to the helmet 104. Anti-slip stripping is applied to the headstrap 216. Referring now to the lens track 215; lens track 215 preferably comprises a recess in a front portion of the goggle-frame 214 allowing the at least one removable lens 120 to be removably attached to the main lens 122 on the goggle-frame 214.

In describing a third embodiment, a goggle system 300 is disclosed herein comprising: a 180 degree view goggle 212 having a goggle-frame 214 including a lens track 215 comprising rigid, yet flexible rubber, and vent ports 117 and optionally vent-port covers 118, a main lens 122, a headstrap 216 comprising an applied flexible anti-slipping means, and a plurality of sequentially stacked removable lens 120. The 180 degree view goggle 212 comprises in functional combination the goggle-frame 214, the main lens 122, the headstrap 216, and the plurality of sequentially stacked curved removable lens 320. The lens track 215 provides a mount for the main lens 122; the main lens 122 having the plurality of sequentially stacked curved removable lens 320 coupled thereto for removal during sport-use. The vent ports 117 preferably comprise breathable foam. The vent-port covers 118 are useful during inclement conditions to prevent water from entering from a top of the 180 degree view goggle 212. The headstrap 216 couples the 180 degree view goggle 212 to a helmet 104 of a wearer-user 140 such that the wearer-user 140 can individually tear-remove each of the at least one plurality of sequentially stacked curved removable lens 320 sequentially as desired approaching the main lens 122 as sequentially removed, as shown in FIG. 1 during an in-use condition 150.

The lens track 215 in goggle system 300 also preferably comprises a recess in the front of the goggle-frame 214. Each of the plurality of sequentially stacked curved removable lens 320 comprises a folded-under finger-tab 130 that only becomes accessible for pulling-removal once an adjacent curved removable lens 320 is removed from the plurality of sequentially stacked curved removable lens 320. The stacked curved removable lens 320 comprises a pre-curved form which provides for accurate views of the sport by the wearer-user 140. This promotes safety during the sport.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A 180 degree view goggle system, comprising:
    a removable goggle lens system, the removable goggle lens system comprising:
        a sequentially-stacked set of lenses, wherein each one of the sequentially-stacked set of film lenses are made of a film and wherein each one of the sequentially-stacked set of lenses are removably fused with an adjacent one of the sequentially-stacked film lenses, each of the sequentially-stacked film lenses comprising;
            a front-face,
            a back-face,
            a thickness, and
            a finger-tab protruding outward from its corresponding sequentially-stacked film lens;
        wherein each of the film lenses is defined by said front-face, said back-face, said front-face, and said back-face separated by said thickness, and said finger-tab formed as an extension of said thickness such that a wearer-user removes each of the film lenses sequentially as desired approaching a main lens of a host goggle as sequentially removed; and
        a main lens formed to provide a 180 degree view to a person wearing the 180 degree view goggle system, wherein a last one of the sequentially-stacked film lenses is removably fused to an outside surface of the main lens; and
    a goggle-frame assembly, the goggle-frame assembly comprising;
        a goggle frame configured to receive the removable goggle lens system; and
        a lens track secured to the goggle frame, the lens track comprising one of a rigid material and a flexible rubber material that secures the finger-tabs of the sequentially-stacked film lenses,
    wherein each of the main lens and the sequentially-stacked film lenses comprises a pre-curved form that matches a curved form of the goggle frame so that the removable goggle lens system is secured to the goggle-frame assembly in response to securing the finger-tabs to the lens track.

2. The removable goggle lens system of claim 1, wherein said film lenses are a transparent-laminate and said finger-tab is folded under said back-face until a top-placed adjacent said film lens is removed from use whereby said finger-tab then becomes accessible for pulling.

3. The removable goggle lens system of claim 1, wherein a terminal one of the sequentially-stacked film lenses is film-fused directly to said main lens.

4. The removable goggle lens system of claim 1, wherein the sequentially-stacked film lenses are a transparent-laminate film.

5. The removable goggle lens system of claim 1, wherein said finger-tab comprises an aperture.

6. The removable goggle lens system of claim 1, wherein said finger-tab is a pull-tab.

7. The removable goggle lens system of claim 1, wherein said finger-tab rotates from adjacent said back-face towards said front-face when unfolded for next-use.

8. The removable goggle lens system of claim 7, wherein an unfolding rotation ends when said finger-tab has rotated to be substantially parallel to said main lens.

9. The removable goggle lens system of claim 1, wherein said sequentially-stacked film are removed from said host goggle via a tearing-action.

10. A 180 degree goggle system, comprising:
    a goggle-frame assembly including;
        a goggle frame;
        a lens track, secured to the goggle frame, and comprising one of a rigid material and flexible rubber material;
    a removable goggle lens system, comprising:
        a plurality of sequentially-stacked film lenses, wherein each one of the sequentially-stacked film lenses are made of a film and are removably fused with an adjacent one of the sequentially-stacked film lenses such that the sequentially-stacked film lenses comprises a layered tear-off stack of film lens;
        a plurality of finger-tabs, wherein each one of the finger-tabs protrudes outward from its corresponding sequentially-stacked film lens; and
        a main lens; and
    a headstrap,
    wherein said lens track secures the finger tabs of the sequentially-stacked film lenses and said main lens, said main lens having said plurality of sequentially-stacked film lenses coupled thereto for removal during sport-use;
    wherein the main lens and the sequentially-stacked film lenses are fused together as a single component; and
    wherein said headstrap couples said 180 degree view goggle to a helmet of a wearer-user such that said wearer-user tear-removes each of the at least one removable film lens sequentially as desired approaching said main lens as said at least one removable film lens are sequentially removed one by one.

11. The removable goggle lens system of claim 10, the goggle-frame assembly further comprising vent ports.

12. The removable goggle lens system of claim 11, wherein said vent ports of the goggle-frame assembly comprise breathable foam.

13. The removable goggle lens system of claim 12, wherein said vent ports of the goggle-frame assembly further comprise vent-port covers useful during inclement conditions to prevent water from entering from a top of said 180 degree view goggle.

14. The removable goggle lens system of claim 10, further comprising a layered foam pad attached to said goggle-frame suitable for wicking moisture to promote comfort of said wearer-user.

15. The removable goggle lens system of claim 10, wherein said headstrap comprises an anti-slip strip to prevent slippage relative to the helmet.

16. The removable goggle lens system of claim 10, wherein an anti-slip stripping is applied to said headstrap.

17. The removable goggle lens system of claim 10, wherein said lens track comprises a recess in a front of said goggle-frame allowing said at least one removable film lens to be removably attached to said main lens on said goggle-frame.

18. A goggle system, comprising:
a 180 degree view goggle assembly, comprising;
a goggle-frame including;
a lens track, secured to the goggle frame, and comprising one of a rigid material and a flexible rubber material, wherein the lens track provides a tear-off tab track delivery system for holding folded tabs during operation and thus only allowing a single unfolded layer of film lens to be exposed and allowing a user of the goggle system to only remove that exposed single layer of film lens from the goggle-frame, thus eliminating the user from accidently grabbing an entire layered stack of film lens from the goggle-frame; and
vent ports and vent-port covers; and
a headstrap comprising an applied flexible anti-slipping means;
a removable goggle lens system, comprising:
a plurality of sequentially-stacked film lenses, wherein each one of the sequentially-stacked film lenses are made of a transparent film and are removably fused with an adjacent one of the sequentially-stacked film lens such that the sequentially-stacked film lenses comprises a layered tear-off plurality of film lens;
a plurality of finger-tabs, wherein each one of the finger-tabs protrudes outward from its corresponding sequentially-stacked film lens; and
a main lens,
wherein said lens track secures said main lens and said plurality of sequentially stacked removable lens to said goggle-frame, said main lens having said plurality of sequentially stacked removable lens coupled thereto for removal during sport-use;
wherein said vent ports comprise breathable foam;
wherein said vent-port covers are useful during inclement conditions to prevent water from entering from a top of said 180 degree view goggle; and
wherein said headstrap couples said 180 degree view goggle to a helmet of a wearer-user such that said wearer-user individually tear-remove each of the at least one plurality of sequentially stacked removable lens sequentially as desired approaching said main lens as sequentially removed.

19. The removable goggle lens system of claim 18, wherein said lens track comprises a recess in a front of said goggle-frame.

20. The removable goggle lens system of claim 18, wherein each of the plurality of sequentially stacked removable lens comprises a folded-under finger-tab that only becomes accessible for pulling-removal once an adjacent said removable lens is removed from said plurality of sequentially stacked removable lens.

* * * * *